(12) United States Patent
Brown et al.

(10) Patent No.: US 10,940,060 B2
(45) Date of Patent: Mar. 9, 2021

(54) SEAL RING CAST PROTECTOR

(71) Applicant: Brownmed, Inc., Spirit Lake, IA (US)

(72) Inventors: Ivan E. Brown, Boston, MA (US);
Ronald Crowley, Spirit Lake, IA (US);
Matthew Garver, Belmont, MA (US);
Teryle Kounkel, Spirit Lake, IA (US);
Brandon Rodriguez, Natick, MA (US)

(73) Assignee: Brownmed, Inc., Boston, MA (US)

( * ) Notice: Subject to any disclaimer, the term of this patent is extended or adjusted under 35 U.S.C. 154(b) by 587 days.

(21) Appl. No.: 14/987,224

(22) Filed: Jan. 4, 2016

(65) Prior Publication Data
US 2017/0189248 A1 Jul. 6, 2017

(51) Int. Cl.
*A61F 15/00* (2006.01)
*A61F 13/04* (2006.01)

(52) U.S. Cl.
CPC .......... *A61F 15/004* (2013.01); *A61F 13/04* (2013.01); *A61F 13/043* (2013.01)

(58) Field of Classification Search
CPC .... A61F 13/043; A61F 13/041; A61F 15/004; A61F 13/04; A61B 46/27; A41D 13/08; A41D 13/081; A41D 19/00
USPC .......... 602/3, 20, 21, 23, 69, 78, 60, 62, 63; 128/856, 82; 2/16, 22, 59, 159; 604/163, 604/164.08, 167.02, 167.06, 338, 339, 604/342; 600/119, 121–125, 186; 623/1.11
See application file for complete search history.

(56) References Cited

U.S. PATENT DOCUMENTS

| | | | | |
|---|---|---|---|---|
| 4,458,680 A | * | 7/1984 | Childers | A62B 17/006 128/201.23 |
| 4,639,945 A | * | 2/1987 | Betz | A61F 15/00 2/22 |
| 6,155,263 A | * | 12/2000 | Weaver | A41D 13/08 128/878 |
| 6,854,459 B1 | * | 2/2005 | Cox | A62B 17/04 128/201.22 |
| 7,434,270 B1 | * | 10/2008 | Bradford | A41D 13/0005 2/159 |
| 7,955,284 B2 | | 6/2011 | Brown et al. | |
| 2004/0199121 A1 | * | 10/2004 | Wenchell | A61B 17/3439 604/167.06 |

* cited by examiner

*Primary Examiner* — Ophelia A Hawthorne
*Assistant Examiner* — Caitlin A Carreiro
(74) *Attorney, Agent, or Firm* — McKee, Voorhees & Sease, PLC

(57) ABSTRACT

A cast and bandage protector that uses a seal ring but avoids water pooling and seepage. It uses a flexible, stretchable and deformable diaphragm stretched tightly over a seal ring in order to seal the ordinarily open end of a flexible sleeve of waterproof material. The rigid seal ring flexible holder holds the flexible sleeve open and the diaphragm tightly stretches over and above it to minimize water pooling seepage and leaking about the interface of the diaphragm and the limb of the patient wearing the cast and the cast protector.

12 Claims, 6 Drawing Sheets

SEAL RING CAST PROTECTOR

FIELD OF THE INVENTION

The invention relates to a cast and bandage protector, for use during showers and baths.

BACKGROUND OF THE INVENTION

Casts have been used for well over a hundred years to protect set, broken bones. There are two basic types of casts: plaster of Paris and more recently, fiberglass. Although more expensive, fiberglass has certain advantages over plaster, such as lighter in weight, generally longer wearing and often more durable.

Regardless of whether a cast is plaster or fiberglass, they typically have cotton padding in their interior facing the patient's skin surface in order to protect the skin and underlying bones from direct contact or pressure caused by the cast. It is important that neither the cast nor the cotton padding get wet. For example, the cast must be kept dry when bathing or showering. Although a fiberglass cast is impervious to water damage, if the cotton lining becomes wet it may cause skin irritation and possible skin breakdown. Also, moisture will cause the skin to become itchy, and the warm moisture may increase the susceptibility to infection. As a result of the above issues, flexible elastic sleeves have been developed which are used to enshroud either the fiberglass or plaster cast. These elastic sleeves are generally known and commonly sold.

Cast protectors that use sealing rings and a gasket have some advantages and some disadvantages. Advantages include ease of application. Disadvantages include increased manufacturing cost and awkward packaging bulk.

To overcome these disadvantages Brownmed developed U.S. Pat. No. 7,955,284, issued Jun. 7, 2011, the disclosure of which is incorporated by reference. In this patent one of the objectives was to eliminate a rigid seal ring. Sale of this device has demonstrated there still is a need for a cast protector with a seal ring as an option for some customers. For some particularly those who have difficulty in application.

Further, in those instances where a seal ring is desired, there is a continuing need to have a seal ring cast protector which allows the water proof bag or flexible sleeve to be placed outside of the seal ring, with the seal ring having an inner edge and outer edge, and the bag open end placed between them with a top membrane surface above the seal ring. This improved lock bag integrity, facilitates automated assembly, and prevents potential problematic water pockets or pools!

Cast protectors, whether using a seal ring or not have ever present problems that need constant attention. A first and important one is the need for effective seals in order to prevent water access to intrude the cast; this often induces designers of cast protectors to use belts, bands and straps that are too tight, with the result being a so-called "tourniquet effect". This of course refers to the seal being so tight that it shuts blood flow. This not only is undesirable, for example with diabetic patients, etc. but does create medical risk and discomfort. A desirable seal is therefore one that is effective, but not too tight.

Additionally seals even if they are effective in the sense that they are not too tight but also effectively seal, must not be seals which allow water paths to form around the interface of the human limb and the sealing gasket. Such water paths present opportunities, especially when taking the cast protector off, allowing water drainage or seepage under the cast and into its inner padding. This inner padding must be kept dry and moisture free or else there are risks of infection, itchiness, and the need to remove the cast and replace it with a dry one.

One such prior sleeve that uses a gasket like diaphragm arrangement is Betz U.S. Pat. No. 4,639,945 issued Feb. 3, 1987. The Betz configuration does not present a true sealing diaphragm; it has lip 33 which as illustrated in FIG. 1, may remain up during use risking an imperfect seal. It also uses a concentric membrane. This is perhaps best illustrated in Betz FIG. 3 which uses tear rings 74, 75 and 76 to enlarge the opening in the central diaphragm or membrane. This further risks leakage or seepage and weak spots.

Accordingly as can be seen, there is a need for a cast protector which has a rigid seal ring and a deformable diaphragm with a central opening made of a different material than the cast protector itself which is stretchable and deformable so that it deforms downwardly and inwardly as a limb is inserted.

A further objective of the present invention is to provide a seal ring deformable diaphragm with a central opening which is stretched tight across the seal ring in drum skin like fashion in order to assure that thrusting insert of the limb deforms a central opening in the diaphragm downwardly and inwardly with just the right amount of tension, and not so much to create a tourniquet.

A yet further objective of the present invention is to provide a seal ring cast protector using a central diaphragm attached to seal ring outer edge and raising above the outer edge as opposed to an interior edge, preferably between an exterior outer edge and bracket or holder edge in order to improve the locking system, avoid water pooling and improve the integrity of the assembly, while facilitating automated assembly.

Further preferential objectives of the invention are to provide finger grips of the rigid seal ring which allow proper placement to enhance gripping by the user for application and if desired thumb pads or thumb placement tabs to assist in applying or removing the cast protector.

Finally, a yet further preferred objective is to provide a seal ring with a logo indicia on it, clearly indicated the front and the back to help the user orient the product correctly without unfolding or needing to look at the cast protector bag.

The method of accomplishing these and other objectives of the invention will become apparent from the detailed preferred description of the invention which follows.

SUMMARY OF THE INVENTION

A cast and bandage protector that uses a seal ring but avoids water pooling and seepage. It uses a flexible, stretchable and deformable diaphragm stretched tightly over a seal ring in order to seal the ordinarily open end of a flexible sleeve of waterproof material. The rigid seal ring flexible holder holds the flexible sleeve open and the diaphragm tightly stretches over it to eliminate water pooling seepage and leaking about the interface of the diaphragm and the limb of the patient and to eliminate pooling on the diaphragm surface.

DETAILED DESCRIPTION OF THE PREFERRED EMBODIMENTS

Figure 1:
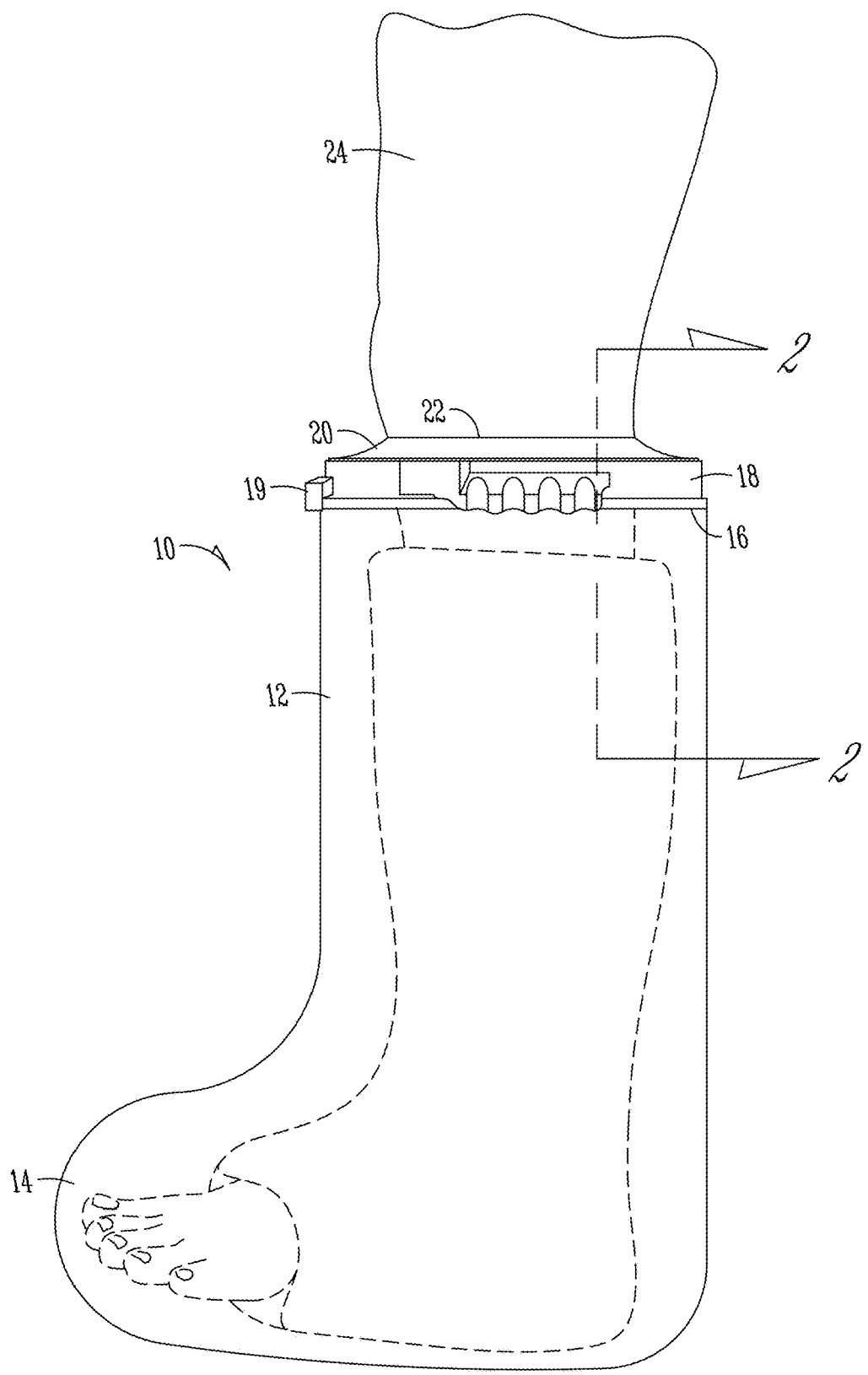
FIG. 1 illustrates a patient's limb surrounded by the protective cast and bandage protector as it might for example be worn in the shower.
Figure 2:
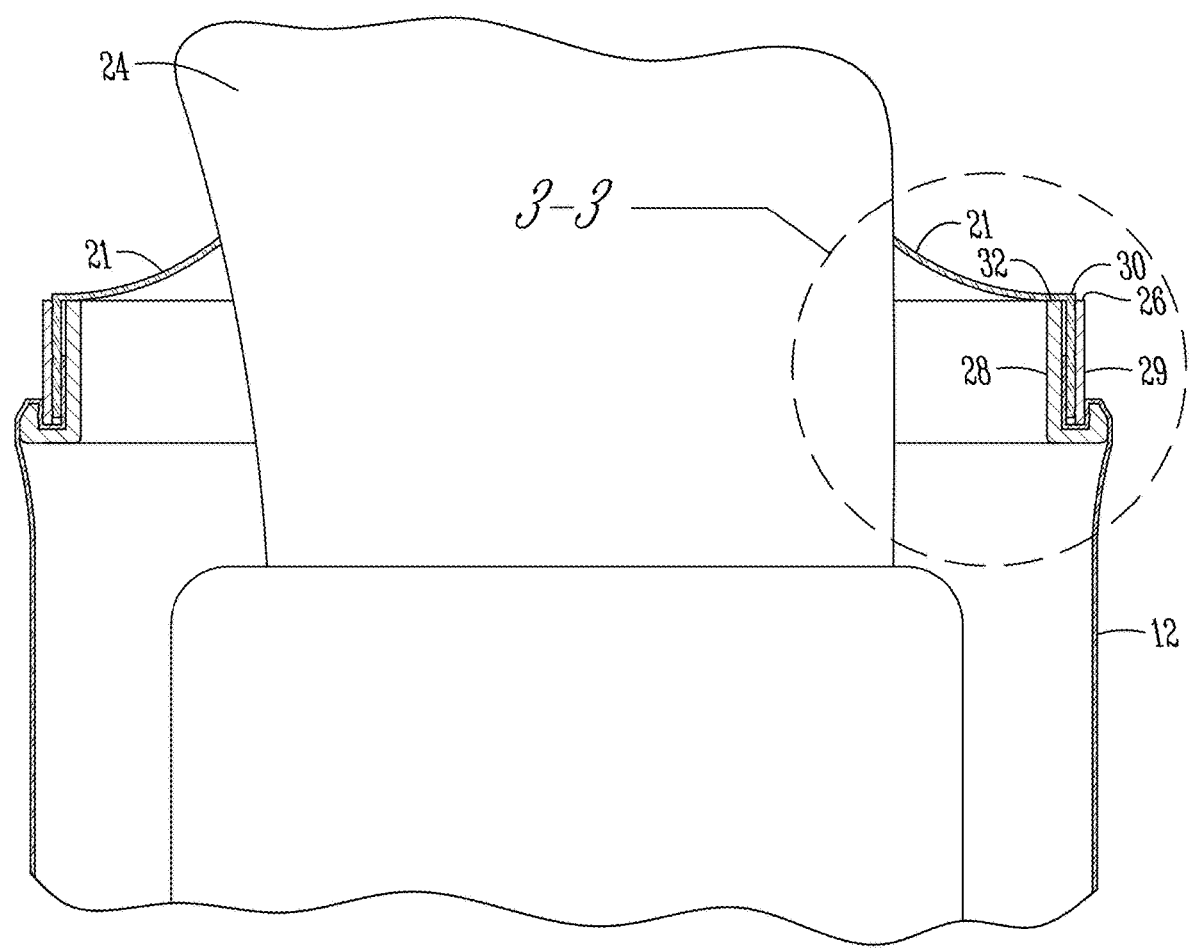
FIG. 2 illustrates a section on line -2-2- of FIG. 1.

FIG. 1 shows a perspective view of the cast on a patient's limb (leg, 24) with a cast proctor 10. Cast protector 10 is comprised of a flexible waterproof sleeve 12 closed at one end, i.e. a foot end 14 of a boot like configuration and having an opened end 16. At open end 16 is an attached seal ring unit 18. Seal ring unit 18 is attached to the upper end of the cast cover sleeve 12 opposite the foot end 14 and is also attached to flexible and stretchable and deformable continuous single surface diaphragm 20 which fits tightly across the top of seal ring unit 18 with a top surface 21 above the top edge of the seal ring unit 18. Diaphragm 20 has a yieldable and deformable central opening 22 and presents a smooth continuous surface 21 to enhance water run-off. For clarity, numeral 18 refers to the entire seal ring unit and 28 refers to the inner ring only and 29 to the outer ring.

As the patient's limb 24 is thrust into cast protector 10 through diaphragm central opening 22 it deforms and pushes in the side edges of diaphragm which upon adjustment open up as illustrated at 22 in FIG. 1.

Worthy of note is that with the cast protector 10 in place as illustrated in FIG. 1 side edges of diaphragm opening 22 are stretched downwardly and inwardly initially but pull up sealingly against limb 24 of the patient. Further, because the diaphragm is tight across the top of seal ring unit 18 and above the outer seal ring 29 top edge 26 there are no creases, wrinkles or folds where water can pool or seep through the seal, instead it simply runs off the tight upper surface 21 of the diaphragm 20, and away from the limb 24.

The sleeve cover 12 at its open end 16 is placed over the inner ring 28 of seal ring unit 18 and the sleeve cover 12 is forced into lock of 28, 29. Finger grips 34, 36 help in putting on the cover protector 10. The thumb pads 38 also assist in putting on cover 10. The diaphragm 20 is stretched across the top of seal ring unit 18 and folded over (30) and held in place across the top of edge 28 between inner ring 28 and outer ring 29. Attachment can be by mechanical snap in of the rings, or adhesive, hot melting, etc. The placement of the (vinyl) bag cast cover 12 between the inner ring 28 and outer ring 29 is important and is a new design feature in comparison of the prior cast protectors. There are two distinct advantages to this design change: inner ring 28 at the inside of the bag cover sleeve 12 and aligning the inner ring/bag for final assembly is easier to accomplish using automated methods and placement of the bag over the inner ring 28 and folding the bag under the bottom edge of outer ring 29 is superior to interior attachment. Second, since the new design is wrapped around and between the inner/outer ring locking system it improves the integrity of the assembly.

Figure 3:
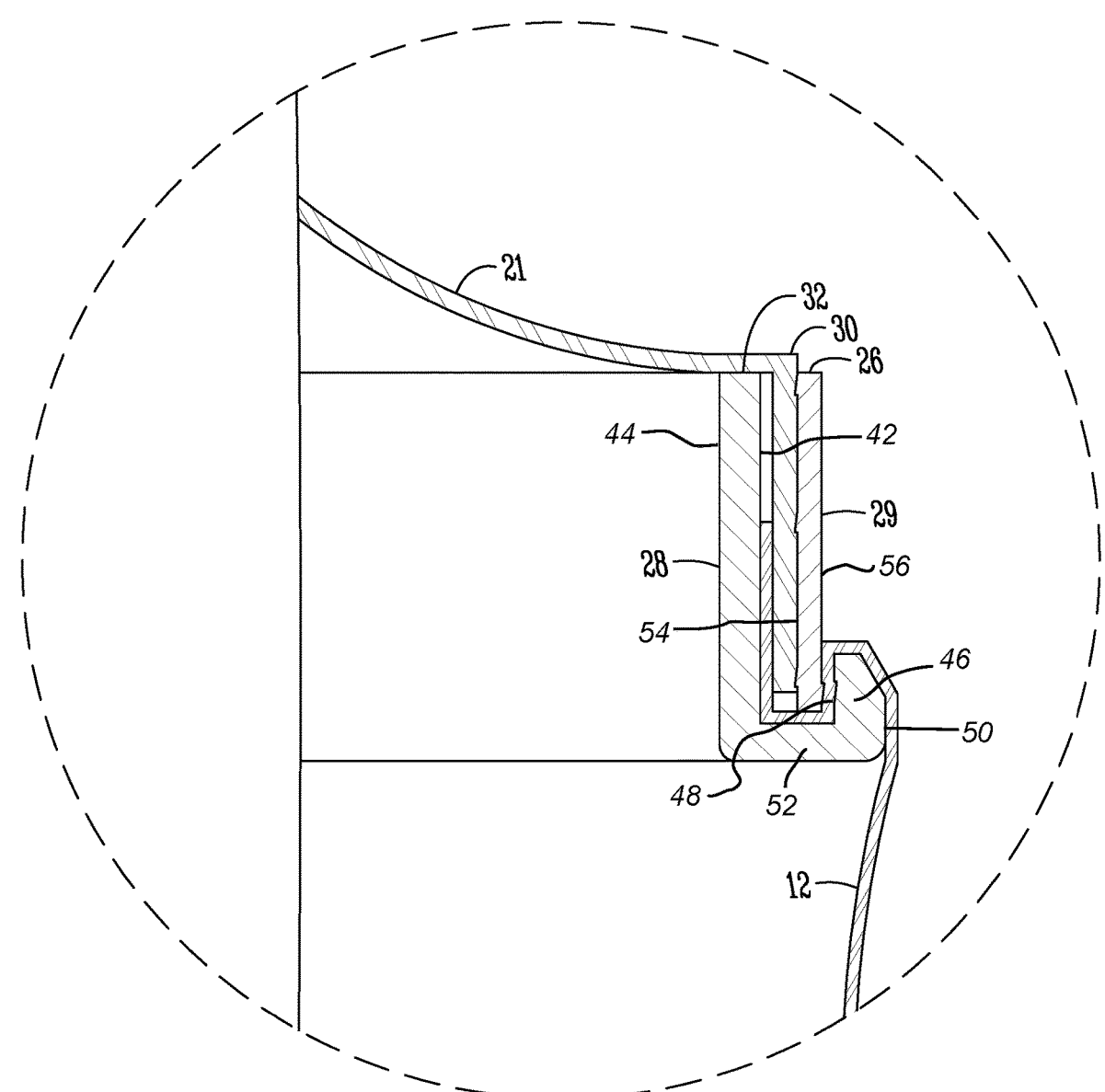
FIG. 3 is a partially broken away partially sectioned and enlarged schematic view of the device of FIG. 1 (see circle of FIG. 2) to illustrate the relationship of the seal ring, sealing diaphragm with top membrane surface above the seal ring.
Figure 4:
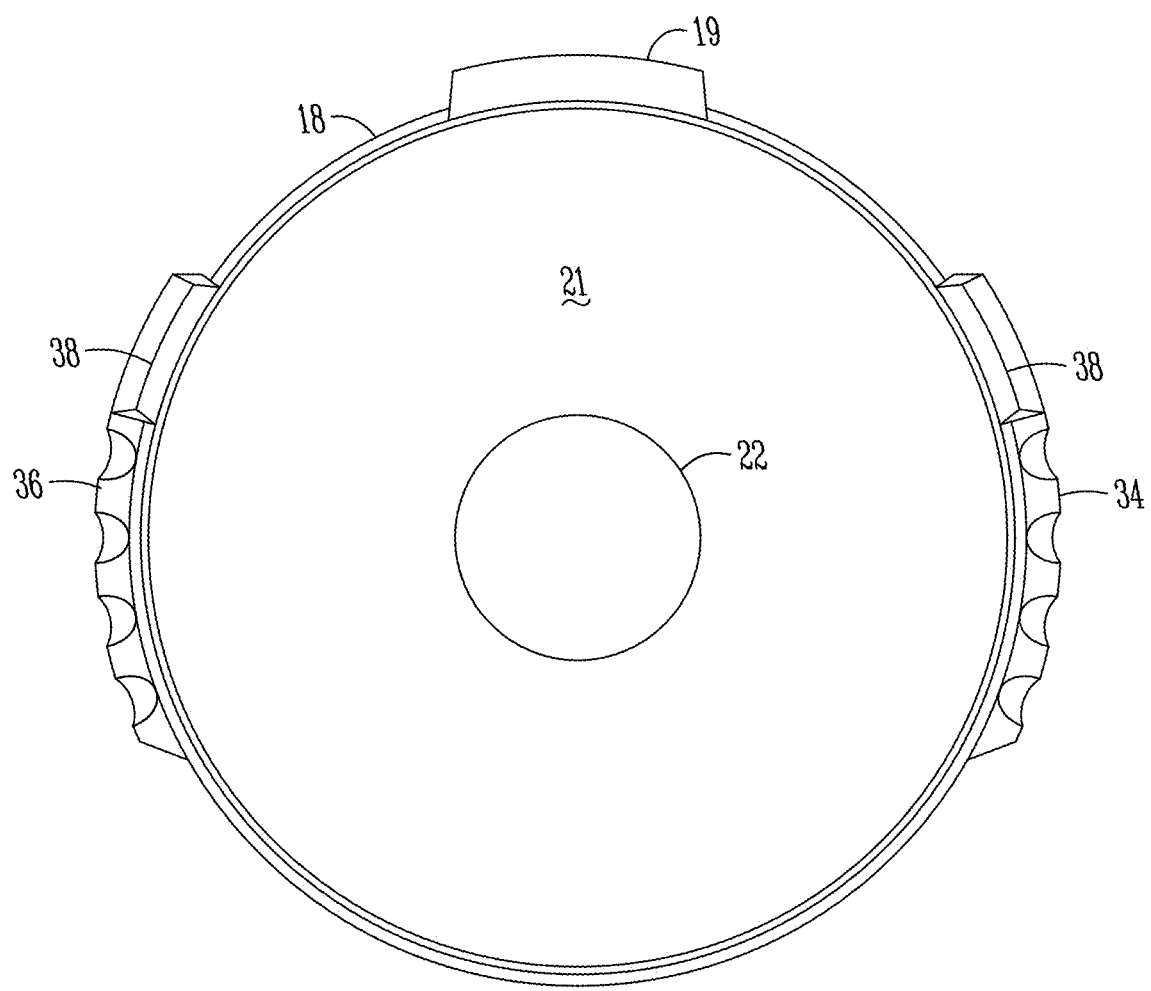
FIG. 4 is a plan view of the seal ring with the diaphragm attached.
Figure 5:
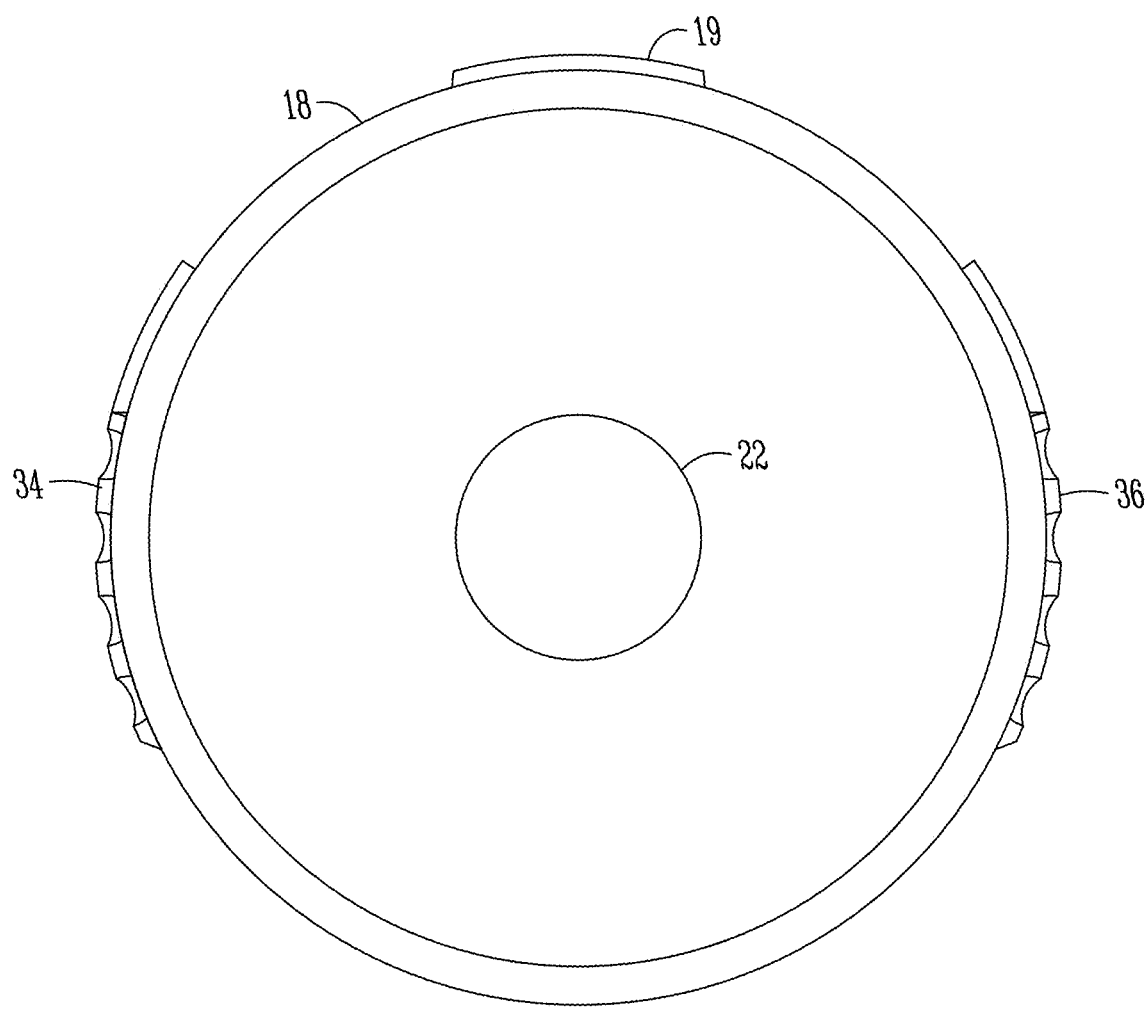
FIG. 5 is a bottom view of the seal ring with the details of attachment of cast protector shown, but with most of the cast protector broken away.
Figure 6:
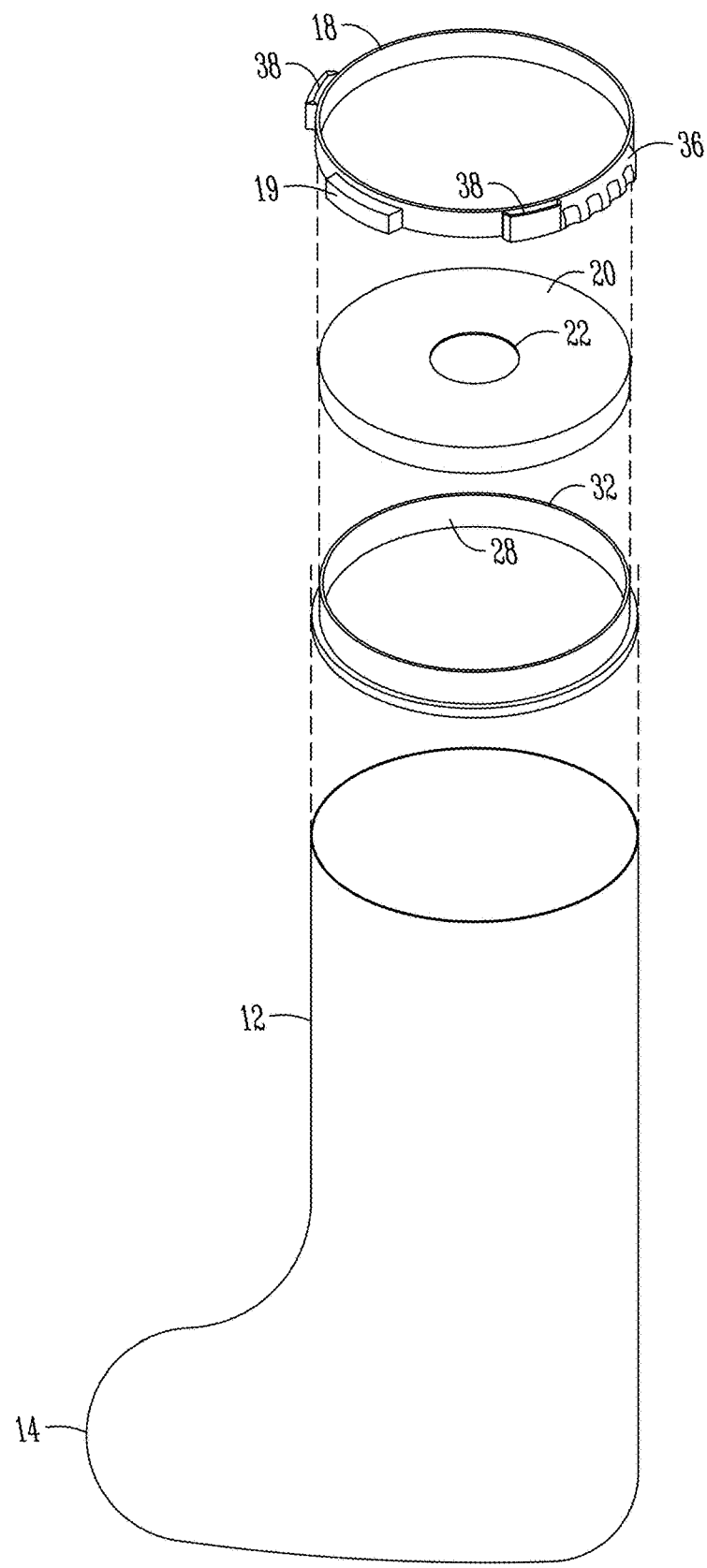
FIG. 6 is an exploded view of the cast protector to best show how the parts fit together.

As seen in FIG. 3, the inner ring 28 has an upright wall 32 with an inner surface 44 adapted to face a wearer's limb and an outer surface 42 that faces away from the wearer's limb. A lower brim 52 extends outwardly from a lower end of the upright wall 32, and a lip 46 extends upwardly from the lower brim 52. The lip 46 has an outer surface 50 facing away from the upright wall 32 and an inner surface 48 facing the upright wall 32. The outer ring 29 has an inner surface 54 surrounding and facing the outer surface 42 of the upright wall 32 of the inner ring 28 and an outer surface 56 facing away from the outer surface 42 of the upright wall 32 of the inner ring 28. The outer ring 29 has a lower portion located between the inner surface 48 of the lip 46 and the outer surface 42 of the upright wall 32 of the inner ring 28.

It is also noteworthy that ring unit 18 may have an outer indicia for example at 19 such as a trademark or company name which helps the user orient the unit in a front facing position, and hold it correctly for putting it on.

The sleeve 12 may be made of any water impermeable polymeric plastic material such as polyolefin films like vinyl, polyethylene, polypropylene, etc. The diaphragm 20 can be made of natural or synthetic rubber material and the seal ring 18, of any light weight semi rigid or rigid plastic.

As previously indicated, the embodiments disclosed in this written specification in detail are preferred and it is to be understood that such embodiments are shown for illustration only and not for purposes of limitation on claims below, which themselves define the metes and bounds of the invention.

What is claimed is:

1. A cast and bandage protector comprising:
   a flexible waterproof sleeve with a closed end and an open end;
   a deformable diaphragm, the diaphragm having a central opening for receiving a wearer's limb;
   a seal ring apparatus for connecting the open end of the waterproof sleeve to the diaphragm in a waterproof connection, the seal ring apparatus comprising an inner ring and an outer ring;
   the inner ring having an upright wall with an inner surface adapted to face the wearer's limb, an outer surface adapted to face away from the wearer's limb, a lower brim extending outwardly from a lower end of the upright wall, and a lip extending upwardly from the lower brim, the lip having an outer surface facing away from the upright wall and an inner surface facing the upright wall;
   the outer ring having an inner surface facing the outer surface of upright wall of the inner ring and an outer surface facing away from the outer surface of the upright wall of the inner ring, the outer ring having a lower portion located between the inner surface of the lip and the outer surface of the upright wall of the inner ring, the lower portion of the outer ring having an outer surface facing the inner surface of the lip;
   wherein the waterproof sleeve wraps around and between the inner and outer rings such that the waterproof sleeve covers the outer surface of the lip of the inner ring and is captured between the inner surface of the lip of the inner ring and the outer surface of the lower portion of the outer ring, the waterproof sleeve further extending under the lower portion of the outer ring and into contact with the outer surface of the upright wall of the inner ring; and
   whereby the diaphragm stretches over an upper end of the upright wall of the inner ring and is captured between the outer surface of the upright wall of the inner ring and the inner surface of the outer ring to tightly and smoothly stretch the diaphragm above the seal ring apparatus to minimize water pooling.

2. The cast and bandage protector of claim 1, wherein the waterproof sleeve is further captured between the diaphragm and the outer surface of the upright wall of the inner ring.

3. The cast and bandage protector of claim 1, wherein the inner ring and the outer ring each comprise semi-rigid or rigid plastic.

4. A cast and bandage protector which minimizes water pooling during use, said protector having a sealing ring and comprising:
   a flexible sleeve of water proof material closed at one end and open at the other end;
   said open other end having a flexible and stretchable deformable diaphragm with a central aperture of a different material than the flexible sleeve sealing and tightly stretched, attached to said other end of said flexible sleeve; and
   a rigid seal ring unit having a rigid inner ring and a rigid outer ring to hold the flexible sleeve and attach said diaphragm, and to tightly and smoothly stretch the diaphragm above a top surface of the seal ring unit to minimize water pooling and seepage about and around the diaphragm; and wherein
      the inner ring has an upright wall with an inner surface adapted to face a wearer's limb, an outer surface adapted to face away from the wearer's limb, a lower brim extending outwardly from a lower end of the upright wall, and a lip extending upwardly from the lower brim, the lip having an outer surface facing away from the upright wall and an inner surface facing the upright wall; and
      the outer ring has an inner surface surrounding and facing the outer surface of the upright wall of the inner ring and an outer surface facing away from the outer surface of the upright wall of the inner ring, the outer ring having a lower portion located between the inner surface of the lip and the outer surface of the upright wall of the inner ring.

5. The cast and bandage protector of claim 4, wherein: the flexible sleeve wraps around and between the inner ring and the outer ring such that the flexible sleeve covers the outer surface of the lip of the inner ring and is captured between the inner surface of the lip of the inner ring and the outer surface of the lower portion of the outer ring, the flexible sleeve further extending under the lower portion of the outer ring and into contact with the outer surface of the upright wall of the inner ring.

6. The cast and bandage protector of claim 5, wherein: the diaphragm stretches over an upper end of the upright wall of the inner ring and is captured between the outer surface of the upright wall of the inner ring and the inner surface of the outer ring to tightly and smoothly stretch the diaphragm above the seal ring unit.

7. The cast and bandage protector of claim 4 wherein the diaphragm is a rubber and is selected from the group consisting of natural and synthetic rubbers.

8. The cast and bandage protector of claim 4 wherein the diaphragm is stretchable and deformable but not so much that in use it creates a tourniquet.

9. The cast and bandage protector of claim 4 wherein the diaphragm has a top surface that is a continuous smooth surface.

10. The cast protector of claim 4 wherein the open end of the flexible sleeve is forced into a lock of the inner and outer ring.

11. The cast and bandage protector of claim 4 wherein the flexible sleeve, and diaphragm are attached to the seal ring unit by snapping in place between the inner and outer rings.

12. A method of forming a cast and bandage protector, the method comprising:
   providing a flexible waterproof sleeve with a closed end and an open end, a stretchable and deformable diaphragm having a deformable central opening for receiving and stretching around a wearer's limb, and a seal ring apparatus comprising an inner ring and an outer ring, wherein the inner ring includes a lower lip that extends outward and upward from a lower end of the inner ring;
   placing the open end of the flexible waterproof sleeve around the lower end of the inner ring;
   stretching the diaphragm around an upper end of the inner ring and capturing the open end of the flexible waterproof sleeve between the inner ring and the diaphragm; and
   placing the outer ring around the diaphragm to thereby capture the diaphragm between the outer ring and the inner ring and to capture the flexible waterproof sleeve between the inner ring and the outer ring with the lower lip surrounding a lower portion of the outer ring.

\* \* \* \* \*